(12) United States Patent
Rizk

(10) Patent No.: US 9,006,162 B1
(45) Date of Patent: Apr. 14, 2015

(54) CLEANSING COMPOSITION WITH INCREASED CONDITIONING EFFECT

(71) Applicant: L'Oreal, Paris (FR)

(72) Inventor: Kirolos Rizk, Helmetta, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/100,117

(22) Filed: Dec. 9, 2013

(51) Int. Cl.
| | |
|---|---|
| C11D 1/02 | (2006.01) |
| C11D 1/66 | (2006.01) |
| C11D 1/83 | (2006.01) |
| C11D 1/88 | (2006.01) |
| C11D 1/94 | (2006.01) |
| A61Q 5/02 | (2006.01) |
| A61K 8/84 | (2006.01) |
| A61K 8/42 | (2006.01) |
| A61K 8/46 | (2006.01) |
| A61K 8/49 | (2006.01) |
| A61K 8/60 | (2006.01) |
| A61Q 5/12 | (2006.01) |

(52) U.S. Cl.
CPC ... A61K 8/84 (2013.01); A61K 8/42 (2013.01); A61K 8/466 (2013.01); A61K 8/494 (2013.01); A61K 8/602 (2013.01); A61Q 5/02 (2013.01); A61Q 5/12 (2013.01)

(58) Field of Classification Search
CPC ............ C11D 1/02; C11D 1/66; C11D 1/662; C11D 1/83; C11D 1/88; C11D 1/94; C11D 3/3769; A61Q 5/02
USPC ......... 510/119, 121, 123, 125, 127, 426, 433, 510/474, 475, 504; 424/70.11, 70.19, 424/70.21, 70.24, 70.31
See application file for complete search history.

(56) References Cited

U.S. PATENT DOCUMENTS

| | | | |
|---|---|---|---|
| 6,110,451 A | 8/2000 | Matz et al. | |
| 6,489,286 B1 * | 12/2002 | Lukenbach et al. | 510/475 |
| 2006/0135382 A1 | 6/2006 | Molenda | |
| 2006/0217283 A1 | 9/2006 | De Salvert et al. | |
| 2011/0139170 A1 * | 6/2011 | Hippe et al. | 132/202 |
| 2011/0155163 A1 | 6/2011 | Viravau et al. | |
| 2011/0155164 A1 | 6/2011 | Viravau et al. | |
| 2012/0196783 A1 | 8/2012 | D'Aversa et al. | |
| 2013/0143784 A1 | 6/2013 | Rizk | |

FOREIGN PATENT DOCUMENTS

| | | |
|---|---|---|
| EP | 1504749 B1 | 12/2008 |
| WO | 20101069500 A1 | 6/2010 |

OTHER PUBLICATIONS

Jorg Kahre, Catherine Le Hen Ferrenbach, Laurence Robbe Tomine, Holger Tesmann, Tensio-Actifs Les alkylpolyglucosides une nouveaute en matiere de soin et de tolerance, Parfums Cosmetiques Actualites No. 131, Nov. 1996, pp. 49-61.
U.S. Appl. No. 14/100,117, filed Dec. 9, 2013, Kirolos Rizk.
U.S. Appl. No. 14/100,126, filed Dec. 9, 2013, Kirolos Rizk.
U.S. Appl. No. 14/100,144, filed Dec. 9, 2013, Kirolos Rizk.
U.S. Appl. No. 14/100,156, filed Dec. 9, 2013, Kirolos Rizk.

\* cited by examiner

*Primary Examiner* — Brian P Mruk
(74) *Attorney, Agent, or Firm* — Novak Druce Connolly Bove + Quigg LLP

(57) ABSTRACT

The present invention is directed to a cleansing composition containing:
(a) from about 6% to about 20% of at least one nonionic surfactant;
(b) from about to about 10% of at least one amphoteric surfactant;
(c) from about 2% to about 8% of at least one anionic surfactant; and
(d) from about 0.01% to about 5% of at least one cationic conditioning polymer;

wherein the amount of nonionic surfactant (a) present in the final composition is greater than the amount of the amphoteric surfactant (b), and the ratio of nonionic surfactant (a) to anionic surfactant (c) is at least 1.9, based on the weight percent of each surfactant in the final composition.

19 Claims, No Drawings

CLEANSING COMPOSITION WITH INCREASED CONDITIONING EFFECT

TECHNICAL FIELD

The present invention relates to personal cleansing compositions. More particularly, the invention relates to a shampoo composition having not only exceptional cleaning effect, but also improved conditioning properties.

BACKGROUND OF THE INVENTION

Conventional cleansing compositions such as shampoos, for example, contain standard surfactants such as anionic, nonionic and/or amphoteric type surfactants in amounts such that the anionic surfactant is typical present in the highest concentration of the foregoing three surfactants. This is because these anionic surfactants provide optimal foaming to the final composition. While nonionic surfactants are also often used in the cosmetic industry as they offer good cleansing, solubilizing and dispersing properties and are less irritating than anionic surfactants, their usage is typically limited to the secondary surfactant by percent in comparison to anionic surfactants due to their poor foaming ability as well as providing lower viscosity to the overall composition (i.e. the composition is thinner and more runny with increased amounts of the nonionic surfactant).

These cleaning compositions can be applied onto a wet keratinous substrate (e.g. hair or skin) and the lather they generate make it possible, after rinsing with water, to remove the diverse types of soils typically present on the hair or skin.

While these composition provide good cleansing power, they often have poor intrinsic cosmetic properties due to the fact that the relatively aggressive nature of such a cleansing treatment may, in the long term, give rise to more or less pronounced damage on hair fibers or skin associated, for example, with the gradual removal of the fats or proteins contained in or at their surface.

Thus, in order to improve the cosmetic properties of cleansing compositions, it is now common practice to introduce into these compositions cationic polymers for use as conditioning agents in order to improve the tactile properties of said compositions. The amount of the cationic polymer that can be used in these compositions, however, oftentimes is limited due to strong interaction and affinity of cationic ingredients with anionic cleansing surfactants. This strong affinity and interaction between anionic surfactants and cationic ingredients can lead to the formation of insoluble salts which causes phase separation resulting in unstable formulations. Furthermore the cationic polymers negatively impact the foam quality of the compositions in terms of volume of foam generated as well as the sensorial feel of the foam.

It is an object of the present invention to provide high foaming, effective cleaning compositions for use in personal care that also can provide increased conditioning effects, are stable and cost-effective.

BRIEF SUMMARY OF THE INVENTION

The present invention relates to an aqueous cleansing composition comprising:
(a) from about 6% to about 20% of at least one nonionic surfactant;
(b) from about 3% to about 10% of at least one amphoteric surfactant;
(c) from about 2% to about 8% of at least one anionic surfactant; and
(d) from about 0.01% to about 5% of at least one cationic conditioning polymer;
wherein the amount of nonionic surfactant (a) present in the final composition is greater than the amount of the amphoteric surfactant (b), and the ratio of nonionic surfactant (a) to anionic surfactant (c) is at least about 1.9:1, by weight, based on the weight percent of each surfactant in the final composition.

The present invention is also directed to a process for cleansing and conditioning a keratinous substrate involving contacting the keratinous substrate with the above-disclosed composition.

The present invention is also directed to a method of conditioning a keratinous substrate involving contacting the keratinous substrate with the above-disclosed composition.

The present invention is also directed to a method of increasing the deposition of hydrophobic non-ionic conditioning agents (such as silicones and oils) onto a keratinous substrate involving contacting the keratinous substrate with a non ionic conditioning agent and the composition of the invention.

The present aqueous composition results from the finding that a blend of a specific amount and ratio of cleaning surfactants enables the composition to incorporate an increased amount of conditioning surfactants in comparison to classical cleaning/conditioning compositions. The present composition provides not only good cleansing of keratinous substrates, but also affords foam having good volume and luxurious feel, while at the same time imparting increased conditioning properties onto the substrate all while reducing the amount of anionic surfactant. The composition is clear in appearance and highly viscous.

It is to be understood that both the foregoing general description and the following detailed description are exemplary and explanatory only, and are not restrictive of the invention.

DETAILED DESCRIPTION OF THE INVENTION

The present compositions provide not only good cleansing of keratinous substrates, but also create good and luxuriously feeling foam, while at the same time imparting increased conditioning properties onto the substrate all while reducing the amount of anionic surfactant. When used as shampoos, these compositions have foaming qualities at least comparable to, most often better than, traditional shampoos, even though they use nonionic surfactants as the primary surfactants and anionic surfactants only as tertiary surfactants. Also, because the compositions use an nonionic surfactant as the primary surfactant, the compositions have lower irritation potential as compared to traditional anionic-rich cleaning compositions.

Moreover and quite unexpectedly, these compositions are stable even with high concentrations of cationic conditioners and even when the cationic conditioners are themselves highly charged. These compositions thus afford increased delivery of cationic conditioning agents in comparison to traditional anionic-based cleaning compositions. When used as shampoos, these compositions deliver conditioner to the hair in a manner in which the conditioner clings to and stays on the hair even after repeated washings. This is believed to be due to the higher quantity of nonionic surfactant in the composition which allows for better compatibility with the cationic agent and improves overall stability in contrast to classical shampoos. This is true even with highly charged cationic polymers (e.g. polyquaternimum-6 (PQ-6)), which has a charge density greater or equal to 6.00 meq/g). Such highly charged polymers have limited compatibility with traditional shampoo compositions due to the strong charge attraction and high degree of complexing between cationic polymer and anionic cleaning surfactants which can lead to formation of insoluble salts resulting in unstable compositions. Thus, the lower degree of complexing in the current compositions allows for the cationic conditioners to be incorporated in the present compositions at higher concentrations (e.g. 1% or more) than in traditional shampoos (which typically contain from about 0.05% to about 0.5% highly charged cationic conditioners) and still remain stable even at elevated (e.g. 45° C.) or reduced temperatures (e.g. 4° C.). It also allows for greater deposition of the cationic polymer onto anionicly charged hair fibers. These compositions thus provide for greater conditioning effect than traditional shampoos thereby minimizing the need for additional conditioning agents such as silicones, yielding overall cost savings.

All percentages and ratios are calculated by weight unless otherwise indicated. All percentages are calculated based on the total composition unless otherwise indicated.

As used herein, all ranges provided are meant to include every specific range within, and combination of sub ranges between, the give ranges. Thus, a range from 1 to 5, includes specifically 1, 2, 3, 4 and 5, as well as 2-5, 3-5, 2-3, 2-4, 1-4, etc.

"A" and "the" as used herein are understood to encompass the plural as well as the singular.

"About" as used herein means within 10% of the indicated number (e.g. "about 10%" means 9%-11% and "about 2%" means 1.8% -2.2%).

At least one as used herein means one or more and thus includes individual components as well as mixtures/combinations.

"Clear" as used herein means that the composition is visually clear (a person is able to see through the composition with their naked eyes). It also means that the composition does not exhibit phase separation. The clarity of a formulation can be measured by the transmittance percentage of light with a wavelength of 700 nm by UV-Visible spectrophotometry. "Clear" samples allow for transmittance of about 60% or higher, more preferably about 70%, even more preferably about 80% or higher, of the light to pass through the formula.

"Conditioning" as used herein means imparting to hair at least one property chosen from compatibility, manageability, moisture-retentivity, luster, shine, and softness. The state of conditioning is evaluated by measuring, and comparing the ease of combing of the treated hair in contrast with the untreated hair.

"Comprising" as used herein is used in the inclusive sense of "having" or "including" and not in the exclusive sense of "consisting only of."

"Good foam" means that the foam produced is in high quantity and is stable and creamy over the period of use.

"HLB" as used herein means the hydrophilic-lipophilic balance of a molecule. It is the ratio between the hydrophilic part and lipophilic part of a molecule. This term is well known to those skilled in the art. See, e.g., "The HLB System: A Time-saving Guide to Emulsifier Selection" (Pub: ICI Americas Inc., 1984) and US2006/0217283 at [0053], both of which are herein incorporated by reference.

"Keratinous substrates", as used herein, include but are not limited to, skin, hair, lips, eyelashes and nails. A Preferred keratinous substrate is hair.

In an embodiment, the invention relates to an aqueous cleansing composition comprising:
(a) from about 6% to about 20% of at least one nonionic surfactant;
(b) from about 3% to about 10% of at least one amphoteric surfactant;
(c) from about 2% to about 8% of at least one anionic surfactant; and
(d) from about 0.01% to about 5% of at least one cationic conditioning polymer;

wherein the amount of nonionic surfactant (a) present in the final composition is greater than the amount of the amphoteric surfactant (b), and the ratio of nonionic surfactant (a) to anionic surfactant (c) is at least about 1.9:1, by weight, based on the weight percent of each surfactant in the final composition.

Nonionic Surfactants (Component (a))

Non-ionic surfactants, while they are known for good cleaning properties, are not preferred in commercial shampoos in part as they are typically too harsh and drying on keratinous substrates (e.g. hair). However, the ratio of this surfactant to and its association with the amphoteric surfactant of the invention enables the use of non-ionic surfactants in the current cleansing formulation and still yield a conditioning effect.

The at least one nonionic surfactant useful in the cosmetic compositions disclosed herein is selected from: alkyl polyglucosides; ethylene glycol, propylene glycol, glycerol, polyglyceryl esters and their ethoxylated derivatives (herein jointly referred to as "glycol ethers"); as well as amine oxides; and mixtures the foregoing.

Alkyl polyglucosides useful in the compositions of the invention include those having the following formula (I):

$$R^1-O-(R^2O)n\text{-}Z(x) \qquad (I)$$

wherein
$R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Such alkyl poly glucoside compounds include lauryl glucoside, octyl glucoside, decyl glucoside, coca glucoside, sucrose laurate, caprylyl/capryl glucoside, and sodium lauryl glucose carboxylate, and mixtures thereof. Typically, the at least one alkyl poly glucoside compound is selected from the group consisting of lauryl glucoside, decyl glucoside and coca glucoside, and more typically lauryl glucoside.

Non-limiting examples of glycol esters useful in the compositions of the invention include those described in M. R. Porter et al., Handbook of Surfactants, Ch. 7, §7.12, pp. 231-235 ($2^{nd}$ Ed. 1994), which is herein incorporated by reference. Preferred glycol esters have HLB values between about 9 and about 18. Particular glycol esters useful in the compositions of the invention include PEG-8 glyceryl laurate, polysorbate-40, polyglyceryl-5 laurate, and mixtures thereof.

Amine oxides useful in the compositions of the invention include those having the formulas (IIA) and (IIB)

$$R-N(CH3)_2-O \qquad \text{(IIA), and}$$

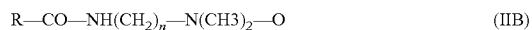

$$R-CO-NH(CH_2)_n-N(CH3)_2-O \qquad \text{(IIB)}$$

wherein
R is an alkyl group having 8-18 carbon atoms; and
n is an integer from 1 to 3.

A non-limiting example of a particular amine oxide is lauramine oxide.

In the present compositions, the at least one nonionic surfactant is used in an amount of from about 6% to about 20%, typically from about 7% to about 10%, and more typically about 7.15%, including all ranges and sub ranges therebetween, by weight based on the total weight of the composition as a whole.

Amphoteric Surfactant (Component (b))

The at least one amphoteric surfactant useful in the cosmetic compositions disclosed herein is chosen from betaines, sultaines, amphoacetates, amphoproprionates, and mixtures thereof. More typically, betaines and amphoproprionates are used, and most typically betaines. Betaines which can be used in the current compositions include those having the formulas (III A-D) below:

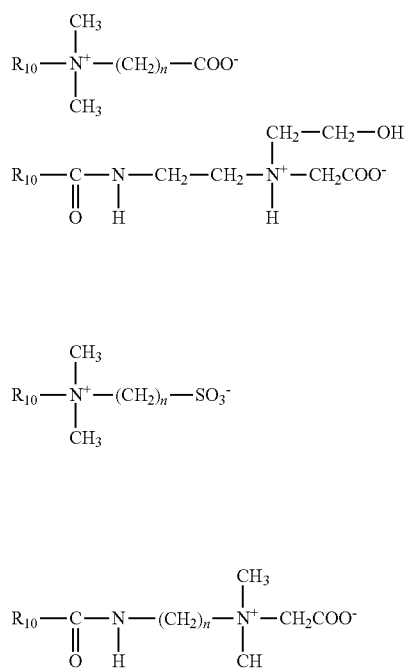

wherein $R^{10}$ is an alkyl group having 8-18 carbon atoms; and n is an integer from 1 to 3.

Particularly useful betaines include, for example, coca betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coca betaine, cocoamidopropyl betaine, behenyl betaine, capryl/capramidopropyl betaine, and lauryl betaine, and mixtures thereof, and more typically cocoamidopropyl betaine.

Hydroxyl sultaines useful in the compositions of the invention include the following

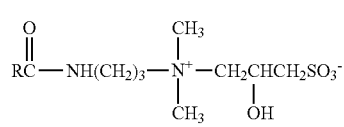

wherein

R is an alkyl group having 8-18 carbon atoms.

Useful alkylamphoacetates include those having the formula (V)

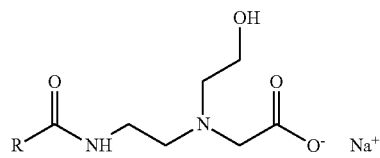

wherein

R is an alkyl group having 8-18 carbon atoms. Useful alkylamphodiacetates include those having the formula (VI)

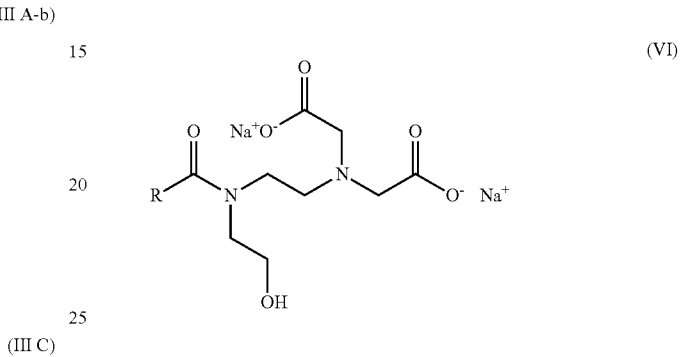

wherein

R is an alkyl group having 8-18 carbon atoms.

In the present compositions, the at least one amphoteric surfactant is used in an amount of from about 3% to about 10% by weight, typically from about 4% to about 8% by weight, and more typically about 5.7% by weight, including all ranges and sub ranges therebetween, based on the total weight of the composition as a whole.

Anionic Surfactant (Component (c))

The at least one anionic surfactant used in the cosmetic compositions disclosed herein can be, for example, chosen from salts, for example, alkali metal salts such as sodium salts, ammonium salts, amine salts, amino alcohol salts and alkaline-earth metal salts, for example magnesium salts, of the following types of compounds: alkyl sulfates, alkyl ether sulfates, acyl isethionates, acyl glycianates, acyl taurates, acyl amino acids, acyl sarcosinates, sulfosuccinates, sulfonates, the alkyl and acyl groups of all these compounds comprising from 6 to 24 carbon atoms (saturated or unsaturated, linear or branched).

Particular sulfate salts useful in the invention include those having the formulas (VII A and B)

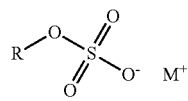

and

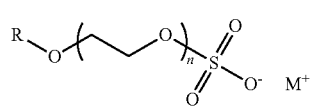

wherein

R is alkyl chain having 6 to 24 carbon atoms;

M is an alkali-metal salt as described above; and
n is an integer from 0 to 3.

Non-limiting examples of acyl amino acids, taurates, isethionate, sulfosuccinates and sulfonates useful in the compositions of the invention include those having the following formulas:

Acyl amino acids:

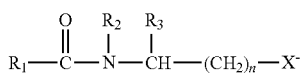
(VIII)

Taurates:

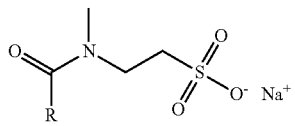
(IX)

Isethionate:

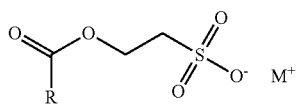
(XA)

and

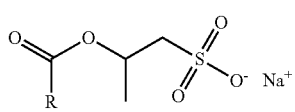
(XB)

sulfosuccinates:

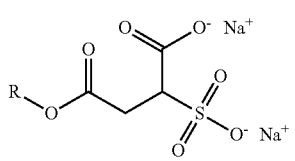
(XI)

Sulfonates:

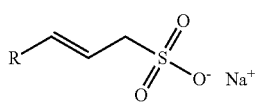
(XII)

wherein in the above formulas
R, $R^1$, $R^2$ and $R^3$ are each independently selected from H or alkyl chain that has 1-24 carbon atoms, said chain being saturated or unsaturated, linear or branched, and X is COO— or $SO_3$—.

Non-limiting examples of alkyl ether sulfates that can be used in the current compositions include lauryl sulfate, laureth sulfate, and salts and mixtures of these. More particularly, the lauryl sulfate is sodium lauryl sulfate and the laureth sulfate is sodium laureth sulfate.

Non-limiting examples of isethionates that can be used in the current compositions include sodium cocoyl isethionate, sodium lauroyl methyl isethionate, and mixtures thereof.

A non limiting example of a taurate that can be used in the current compositions is sodium methyl cocoyl taurate.

Acyl amino acids that can be used in the current compositions include amino acid surfactants based on glycine, sarcosine, threonine, glutamine, glutamic acid or alanine. The most common salt ion attached to the at least one acyl amino acid can be sodium or potassium. Alternatively, the salt attached to the acyl amino acid can be an organic salt such as triethanolamine (TEA) or a metal salt. Examples of acyl amino acid compounds include but are not limited to sodium cocoyl glycinate, potassium cocoyl glycinate, and sodium lauryl sarcosinate, sodium cocoyl alaninate, and salts thereof. Typically, the at least one acyl amino acid is selected from the group consisting of sodium cocoyl glycinate and potassium cocoyl glycinate, and in particular sodium cocoyl glycinate.

A non-limiting example of a sulfosuccinate that can be used in the current compositions is disodium laurel sulfosuccinate.

A non-limiting example of a sulfonate that can be used in the current compositions is sodium C14-16 olefin sulfonate.

The at least one anionic surfactant is present in a total amount ranging from about 2% to about 8% by weight, typically from about 2.5% to about 5%, more typically 3% by weight, including all ranges and sub ranges therebetween, based on the total weight of the composition as a whole.

Cationic Conditioning Polymer (Component (d))

The at least one cationic conditioning agent used in the cosmetic compositions disclosed herein is chosen, for example, from a polymer, including homopolymers and copolymers.

Non limiting examples of polymers that can be used in the current compositions include: cationic cellulose derivatives, such as for example polyquaternium-10 ("PQ-10"); cationic gum derivatives such as for example gum derivatives, including particularly guar hydroxypropyltrimonium chloride; polymer derivatives of diallyldimethyl ammonium chloride ("poly-DADMAs") and of methacrylamidopropyltrimethylammonium chloride ("poly-MAPTACs"), and having the following formulas:

MAPTAC:

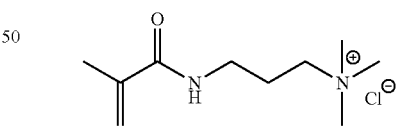

and
DADMAC:

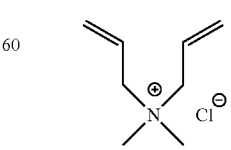

Non-limiting examples of poly-DADMAs and poly-poly-MAPTACs include, polyquaternium-4 (PQ-4), polyquaternium-5 (PQ-5), polyquaternium-6 (PQ-6), polyquaternium-7 (PQ-7), polyquaternium-22 (PQ-22), polyquaternium-37 (PQ-37), polyquaternium-39 (PQ-39), polyquaternium47 (PQ-47) and polyquaternium-53 (PQ-53), particularly DAD-MAC-based polymers, specifically PQ-6 and PQ-22.

Cationic proteins, such as, for example, hydroxypropyltrimonium hydrolyzed wheat protein are also useful as cationic conditioning agents.

In a particular embodiment, the cationic conditioning polymer is selected from PQ 6, PQ-22, and mixtures thereof.

The at least one cationic conditioning polymer is present in the compositions of the invention in an amount of from about 0.01% to about 5% by weight, typically from about 0.1% to about 3% by weight, and more typically from about 0.25% to about 2%, by weight, based on the total weight of the composition as a whole. In a particular embodiment, the amount of cationic conditioning polymer is present at about 1% by weight, based on the total weight of the composition as a whole.

Optional Additives

The composition of the present disclosure may additionally include any other adjuvant or additive that is usually used in the field of self-cleaning products, in particular shampoos. A person skilled in the art would know which adjuvants and/or additives to select to achieve the desired results (e.g. preservatives) without adversely affecting the properties of claimed emulsions. For example, such additives include pH adjusting agents, preserving agents, sequestrants and chelators, consistency regulators (e.g. isopropyl alcohol), thickeners, antioxidants, fragrances, dyestuffs such as soluble dyes and pigments, optical brighteners, electrolytes and stabilizers (e.g. sodium chloride, glycerin), plant extracts, proteins, amino acids, vitamins, glycols, emollients, derivatives of the foregoing, and mixtures thereof. Such additives are described, for example in US2012/0308492 at [0079]-[0080] and US2006/0217283 at [0084]-[0087], both of which are herein incorporated by reference. These additives may be hydrophobic or hydrophilic.

Non-limiting examples of pH adjusting agents include potassium acetate, potassium hydroxide, sodium carbonate, sodium hydroxide, phosphoric acid, succinic acid, sodium citrate, citric acid, boric acid, lactic acid, sodium hydrogen carbonate, ethanol amines, and mixtures thereof. In a particular embodiment, the pH adjusting agent is selected from potassium hydroxide, sodium hydroxide, ethanol amines, and mixtures thereof. In a particular embodiment, the pH adjusting agent is selected from sodium hydroxide, potassium hydroxide and ethanol amines, and mixtures thereof.

Non-limiting examples of useful preservatives include ethanol, polyvinyl alcohol, phenoxyethanol, benzyl alcohol, salicylic acid, sodium benzoate, caprylyl glycol, methyl paraben, propyl paraben, ethylhexylglycerin, 1,3-propanediol, cholrphensin, methylchloroisothiazolinone, methylisothiazolinone, benzalkonium chloride, polyaminopropyl biguanide, and mixtures thereof. In a particular embodiment, the pH adjusting agent is selected from cholrphensin, methylchloroisothiazolinone, methylisothiazolinone, benzalkonium chloride, polyaminopropyl biguanide, and mixtures thereof.

Chelating agents and antioxidants are ingredients which assist in preventing or retarding spoilage. Examples of antioxidants suitable for use in the present composition are potassium sulfite, sodium bisulfite, sodium erythrobate, sodium metabisulfite, sodium sulfite, propyl gallate, cysteine hydrochloride, butylated hydroxytoluene, butylated hydroxyanisole, and mixtures thereof. Suitable chelators include salts of ethylenediaminetetraacetic acid ("EDTA"), butylated hydroxytoluene ("BHT"), and mixtures thereof.

The cleansing compositions of the present invention have a pH of from about 5 to about 9, more typically between about 6 and about 8. Additionally, the cleansing compositions are preferably clear.

The present cleansing composition has a viscosity of about 2500 cPs to about 30000 cPs, typically from about 3000 cPs to about 20,000 cPs, more particularly from about 3000 cPs to about 6000 cPs, and more particularly from about 3000 cPs to about 6000 cPs, including all ranges and sub ranges therebetween, measured using Brookfield viscometer as discussed below in the examples.

In an embodiment, the present invention relates to an aqueous cleaning and conditioning composition comprising:
  (a) from about 6% to about 20% of at least one nonionic surfactant selected from alkyl polyglucosides and glycol esters, and mixtures thereof;
  (b) from about 3% to about 10% of at least one amphoteric surfactant selected from betaines, sultaines, amphoacetates and amphoproprionates, and mixtures thereof;
  (c) from about 2% to about 8% of at least one anionic surfactant selected from lauryl sulfates, laureth sulfates, isethionates, glutamates, alaninates, glycinates, taurates, acyl amino acids, sarcosinates, sulfosuccinates, sulfonates, alkyl polyglucoside sulfonates and alkyl polyglucoside carboxylates, and mixtures thereof; and
  (d) from about 0.01% to about 5% of at least one cationic conditioning polymer;
  wherein the amount of nonionic surfactant (a) present in the final composition is greater than the amount of the amphoteric surfactant (b), and the ratio of nonionic surfactant (a) to anionic surfactant (c) is at least about 1.9:1, by weight, based on the weight percent of each surfactant in the final composition.

In an embodiment, the ratio of the amount of nonionic surfactant (a) present in the final composition to the amount of anionic surfactant (c) is from about 1.9:1 to about 16:1, more typically from about 2:1 to about 10:1, particularly from about 2:1 to about 5:1, and more particularly about 2:1, including all ranges and sub ranges therebetween.

In a particular embodiment, the present invention relates to an aqueous cleaning and conditioning composition comprising:
  (a) from about 6% to about 20% of at least one nonionic surfactant selected from lauryl glucoside, decyl glucoside, and mixtures thereof;
  (b) from about 3% to about 10% of at least one amphoteric surfactant selected from cocoamphopropionate, cocoamidopropyl betaine, and mixtures thereof;
  (c) from about 2% to about 8% of at least one anionic surfactant selected from sodium cocoyl taurate, sodium cocoyl glycinate, sodium cocoyl taurate, and sodium laureth sulfate, and mixtures thereof; and
  (d) from about 0.01% to about 5% of at least one cationic conditioning polymer;
  wherein the amount of nonionic surfactant (a) present in the final composition is greater than the amount of the amphoteric surfactant (b), and the ratio of nonionic surfactant (a) to anionic surfactant (c) is from about 1.9:1 to about 5:1, based on the weight percent of each surfactant in the final composition.

In a particularly preferred embodiment cationic conditioning agent (d) is selected from polyquaternium-6 (PQ-6) and polyquaternium-22 (PQ-22), and mixtures thereof.

The present invention is also directed to a process for cleansing and conditioning a keratinous substrate involving contacting the keratinous substrate with the above-disclosed cleansing composition. Preferably the keratinous substrate is hair.

It has also been found that the current formulation also increases/improves the deposition of hydrophobic non-ionic conditioning agents, for example silicones and oils, onto a keratinous substrate. Thus, in another embodiment, the invention is also directed to a method of increasing the deposition of hydrophobic non-ionic conditioning agents onto a keratinous substrate comprising contacting the keratinous substrate with a non-ionic conditioning agent and a composition of the invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis unless otherwise specified.

Examples

Preparation

The compositions of the examples below were prepared by adding the nonionic, amphoteric and anionic surfactants to water and mixing while hearing to 50° C. until the mixture was uniform. To the extent used, fragrances, preservatives and conditioning agent(s) were then added. All of the compositions in the examples 1 and 2 were clear gel-like compositions. Depending on the surfactants used, the compositions were colorless, yellow or brownish. Clarity of the compositions was measured by the transmittance percentage of light with a wavelength of 700 nm by UV-visible spectrophotometry.

TABLE 1

Examples 1-5: Compositions Having Various Surfactant Substitutions

| Ingredients category | INCI Names | Ex 1 | Ex 2 | Ex 3 | Ex 4 | Ex 5 |
|---|---|---|---|---|---|---|
| Water, Preservatives, Dyes, Fragrance | | QS | QS | QS | QS | QS |
| Nonionic surfactant (A) | LAURYL GLUCOSIDE | 7.15 | 7.15 | 7.15 | 7.15 | |
| Nonionic surfactant (A) | DECYL GLUCOSIDE | | | | | 7.15 |
| Amphoteric surfactant (B) | COCAMIDOPROPYL BETAINE | 5.7 | 5.7 | 5.7 | | 5.7 |
| Amphoteric surfactant (B) | SODIUM COCOAMPHO-PROPIONATE | | | | 5.7 | |
| Anionic Surfactant (C) | SODIUM COCOYL GLYCINATE | 3 | 3 | | 3 | 3 |
| Anionic Surfactant (C) | SODIUM METHYL COCOYL TAURATE | | | 3 | | |
| Conditioning agent (D) | POLYQUATERNIUM-6 | 1 | | 1 | 1 | 1 |
| Conditioning agent (D) | POLYQUATERNIUM-22 | | 1 | | | |

As is shown above in Examples 1-5, the compositions of the invention can accommodate higher amounts (e.g. 1% or higher) of highly charged cationic polymers (PQ-6 and PQ-22) than is found in currently available commercial shampoo formulations (which typically contain from about 0.05% to about 0.5%) and still remain stable. The quantity of PQ-6 in the currently available commercial shampoo formulations is limited due to adverse complexing interactions between the high cationic charge density of the conditioning polymer and the high quantity of anionic primary surfactants (e.g., sodium laurel sulfate and sodium laureth sulfate) typically found in these commercial shampoo formulations.

Evaluation Protocols

Stability:

The composition of Example 2 was stored at reduced temperatures (4-6° C.), elevated temperatures (37-50° C.) and room temperature for at least 8 weeks. Properties evaluated included visual inspection (phase separation), stability of pH, and stability of acceptable usage viscosity 2000-40,000 cps measured using a Brookfield viscometer. A product was considered stable if it passed all 3 criteria of testing.

The Results for Example 2 are as follows:
Transmittance of light at 700 nm=91%
Initial viscosity: 3500 cps
8 week viscosity: 3255 cps
Appearance: clear and viscous liquid.

Sensorial Tests and Protocols:

The compositions and products were evaluated by trained expert stylist in a blind coded half-head test using touch and visual observation. Evaluations were conducted on 8 models and the ratings were averaged and analyzed. The guideline for each test is as follows.

Flash Foam:

This property is measured at the initial generation stage of the foam. It is a measure of the amount of massaging the consumer needs to input in order to generate foam. The scale is 1 (min effort/good foaming composition) to 5 (max effort/poor foaming composition). Thus, in this test a rating of 1 is preferred and 5 is the poorest rating.

Abundance of Foam:

This is a measure of the overall quantity of the foam. The scale is 1 (low foam) to 5 (high foam). Thus, in this test a rating of 5 is preferred and 1 is the poorest rating.

Airy Foam:

This measurement reflects the density of the foam. The scale from 1 (dense creamy foam like shaving cream) to 5 (airy foam with large bubbles like dawn dishwashing detergent).

Foam Stability:

This is a measure of foam stability after the composition is applied to the scalp (meaning no more scalp massaging). "Stable" foam remains bubbly and abundant while "unstable" foam collapses and starts to disappear. The scale is from 1 (unstable) to 5 (very stable). Thus, in this test a rating of 5 is preferred and 1 is the poorest rating.

Suppleness-Rinsing:

This is one of the measures used to evaluate the conditioning effect of a composition. It is an assessment of the suppleness (bendability) of hair under rinsing water. The scale is 1 (stiff) to 5 (very supple and conditioned). Thus, in this test a rating of 5 is preferred and 1 is the poorest rating.

Ease of Passing Fingers:

This is another measure of the conditioning effect of a composition. It assesses a composition's ability to detangle hair by measuring the amount of work needed to pass fingers through towel dried hair. This attribute is usually achieved by using conditioners and is rarely highly rated by the use of shampoo compositions alone. The scale is 1 (difficult/tangled) to 5 (easy/untangled/conditioned). Thus, in this test a rating of 5 is preferred and 1 is the poorest rating.

Wet Smoothness:

This measures the tactile feel of hair fibers after rinsing. The scale is 1 (hair is rough and stripped) to 5 (hair is very smooth and conditioned). Thus, in this test a rating of 5 is preferred and 1 is the poorest rating.

The results of these tests are summarized in Tables and 3 below. The starred attributes reflect substantial differences with respect to a comparator product.

TABLE 2

Comparison Testing vs. Dove

| Attribute | Example 2 | Dove Intensive repair shampoo |
|---|---|---|
| Flash Foam (1st) (0-5) | 2.75 | 2.88 |
| Abundance of Foam (1st) (0-5) | 2.94 | 3.13 |
| Airy Foam (1st) (1-4) | 2.63 | 2.63 |
| Foam Stability (1st) (1-4) | 3.63* | 2.88 |
| Suppleness - Rinsing (1st) (0-5) | 3.13* | 2.50 |
| Ease of Passing Fingers (1st) (1-4) | 3.00* | 2.38 |
| Wet Smoothness (0-5) | 3.13* | 2.31 |

The results above show that the composition of the invention has comparable foaming to a state of the art anionic-based shampoo, but provides increased conditioning after rinsing.

TABLE 3

Comparison Testing vs. Pantene

| Attribute | Example 2 | Pantene Color Preserve Shine Shampoo |
|---|---|---|
| Flash Foam (1st) (0-5) | 2.50 | 2.50 |
| Abundance of Foam (1st) (0--5) | 2.44 | 3.00 |
| Airy Foam (1st) (1-4) | 2.00 | 3.13 |
| Foam Stability (1st) (1-4) | 2.88 | 2.25 |
| Hair Smoothness in Foam (1st) (1-4) | 3.13 | 2.38 |
| Squeaky Clean (1st) (0-5) | 1.81 | 2.94 |
| Suppleness - Rinsing (1st) (0-5) | 2.88 | 2.00 |
| Ease of Passing Fingers (1st) (1-4) | 3.50 | 2.50 |
| Wet Easy Combing (0-5) | 3.50 | 2.06 |
| Ease of Passing Fingers (1-4) | 3.38 | 2.25 |
| Wet Smoothness (0-5) | 3.25 | 2.38 |

The table above shows that the composition of the invention has flash foaming comparable to a commercial "high foaming" state of the art cleansing shampoo product, but affords improved foam stability and greatly improved conditioning effect as against said product.

Cationic Deposition Study:

Deposition of cationic polymer was studied using an established method in the art referred to as the rubine dye test. The test uses an anionic red dye (red 80) which adsorbs onto the cationic changes left on the hair after rinse. Qualitative or quantitative deposition is determined by the amount of red dye remaining on the hair fibers after rinse.

The protocol for treating and staining the swatches is:
Hair is rinsed under warm water.
Product is applied and lathered for 30 seconds.
Product is rinsed under warm water.
Hair swatches are submerged into dye solution proportional to the weight of the hair swatch and allowed to soak for 30 seconds.
Dye solution is rinsed for 30 second under warm water.
Swatches are allowed to air dry before comparison Hair swatches treated with the composition of Example 2, Pantene and Dove shampoos were subjected to cationic deposition studies following the above protocol. The increased "redness" of the hair in a swatch demonstrates the increased retention of cationic polymer (in the case of Example 2, PQ-22) on to the hair swatch after rinsing. The results of this test are summarized in Table 4 below.

TABLE 4

Cationic Deposition Comparison with Dove and Pantene

| Product | Description of swatch | Result |
|---|---|---|
| Control cleansing shampoo (no cationic conditioner) | Gray hair was unstained | Negative Result - No color (no cationic deposition) |
| Dove intense repair shampoo | Gray hair was unstained | Negative Result - No color (no cationic deposition) |
| Pantene nature fusion shampoo | Gray hair was unstained | Negative Result - No color (no cationic deposition) |
| Pantene anti-break shampoo | Gray hair was unstained | Negative Result - No color (no cationic deposition) |
| Pantene color preserve shine shampoo | Gray hair was stained with very slightly pink shade. The stain was limited to the upper section ("root" end) of the hair watch. | Positive Result - slight color change at the "root" end of swatch (low level of cationic deposition limited to the "root" end of swatch, no deposition at the far end of the swatch) |
| Example 2 with PQ-22 | Gray hair was stained in bright pinkish red shade throughout the swatch | Positive Result - bright pink color throughout the entire hair swatch (highest level of cationic deposition of the tested compositions) |

The data in Table 4 demonstrates that the hair swatch treated with the composition of Example 2 shows the highest level of conditioning effect (highest level of cationic conditioning polymer deposition) in this comparative test.

What is claimed is:

1. An aqueous cleansing composition comprising:
    (a) from about 6% to about 20% of at least one nonionic surfactant that is an alkyl polyglucoside;
    (b) from about 3% to about 10% of at least one amphoteric surfactant that is an amphopropionate, an amphoacetate, or a combination thereof;
    (c) from about 2% to about 8% of at least one anionic surfactant selected from salts of each of alkyl sulfates, alkyl ether sulfates, acyl isethionates, acyl glycinate, acyl taurates, acyl amino acids, acyl sarcosinates, sulfosuccinates, sulfonates, wherein the alkyl and acyl groups of all these compounds comprise from 6 to 24 carbon atoms; and
    (d) from about 0.01% to about 5% of at least one cationic conditioning polymer;
    wherein the amount of nonionic surfactant (a) present in the final composition is greater than the amount of the amphoteric surfactant (b), and the ratio of nonionic surfactant (a) to anionic surfactant (c) is at least 1.9:1, by weight, based on the weight percent of each surfactant in the final composition.

2. The composition of claim 1 wherein the at least one nonionic surfactant (a) is present in the composition in an amount of from about 7% to about 10%, by weight, based on the total of weight of the composition.

3. The composition of claim 2 wherein the nonionic surfactant (a) is selected from lauryl glucoside, decyl glucoside, coco glucoside, and mixtures thereof.

4. The composition of claim 1 wherein the amphoteric surfactant (b) is present in the composition in an amount of from about 4% to about 8%, by weight, based on the total of weight of the composition.

5. The composition of claim 1 wherein the anionic surfactant (c) is present in the composition in an amount of from about 2.5% to about 5%, by weight, based on the total of weight of the composition.

6. The composition of claim 1 wherein the at least one anionic surfactant (c) is selected from sodium lauryl sulfate, sodium laureth sulfate, sodium cocoyl isethionate, sodium lauroyl methyl isethionate, sodium cocoyl glycinate, potassium cocoyl glycinate, sodium lauryl sarcosinate, sodium cocoyl alaninate, sodium cocoyl taurate, sodium methyl cocoyl taurate, sodium cocoyl glycinate, potassium cocoyl glycinate, disodium laurel sulfosuccinate, sodium C14-16 olefin sulfonate, and mixtures thereof.

7. The composition of claim 1 wherein the cationic conditioning polymer (d) is present in the composition in an amount of from about 0.1% to about 3% by weight, based on the total of weight of the composition.

8. The composition of claim 7 wherein the cationic conditioning polymer (d) is selected from polyquaternium-10, guar hydroxypropyltrimonium chloride, polyquaternium-4, polyquaternium-5, polyquaternium-6, polyquaternium-7, polyquaternium-22, polyquaternium-37, polyquaternium-39, polyquaternium-47, polyquaternium-53, and mixtures thereof.

9. The composition of claim 8 further comprising one or more component selected from a pH adjusting agent, a preservative, an antioxidant, a fragrance, a chelating agent, a colorant, and mixtures thereof.

10. The composition of claim 1 having a viscosity from about 3000 cPs to about 6000 cPs.

11. The composition of claim 1 having a pH from about 8 to about 4.5.

12. An aqueous cleaning and conditioning composition comprising:

(a) from about 7% to about 10% of at least one nonionic surfactant that is an alkyl polyglucoside;
(b) from about 4% to about 8% of at least one amphoteric surfactant that is an amphopropionate;
(c) from about 2.5% to about 5% of at least one anionic surfactant selected from sodium cocoyl glycinate, sodium cocoyl taurate, and sodium laureth sulfate, and mixtures thereof; and
(d) from about 0.25% to about 2% of at least one cationic conditioning polymer;
wherein the amount of nonionic surfactant (a) present in the final composition is greater than the amount of the amphoteric surfactant (b), and the ratio of nonionic surfactant (a) to anionic surfactant (c), is from about 2:1 to about 5:1, based on the weight percent of each surfactant in the final composition.

13. The composition of claim 12 wherein the cationic conditioning polymer (d) is selected from polyquaternium-6, polyquaternium-22, and mixtures thereof.

14. A method of cleansing and conditioning hair comprising contacting the hair with a composition according to claim 1.

15. A method of conditioning a keratinous substrate involving contacting the keratinous substrate with the composition of claim 12.

16. A method of increasing the deposition of non-ionic silicone polymers onto a keratinous substrate involving contacting the keratinous substrate with a non-ionic silicone polymer and the composition of claim 12.

17. A method of increasing the deposition of hydrophobic non-ionic conditioning agents onto a keratinous substrate comprising contacting the keratinous substrate with a non-ionic conditioning agent and the composition of claim 12.

18. The composition of claim 1, wherein the at least one anionic surfactant (c) is a sulfate.

19. The composition of claim 12, wherein the at least one anionic surfactant (c) is sodium laureth sulfate.

* * * * *

UNITED STATES PATENT AND TRADEMARK OFFICE
CERTIFICATE OF CORRECTION

PATENT NO. : 9,006,162 B1
APPLICATION NO. : 14/100117
DATED : April 14, 2015
INVENTOR(S) : Kirolos Rizk Page 1 of 1

It is certified that error appears in the above-identified patent and that said Letters Patent is hereby corrected as shown below:

On the title page, in the (57) ABSTRACT, change as follows:

(b) from about 3% to about 10% of at least one amphoteric surfactant;

Signed and Sealed this
First Day of March, 2016

Michelle K. Lee
*Director of the United States Patent and Trademark Office*